(12) United States Patent
Platt et al.

(10) Patent No.: US 11,673,733 B2
(45) Date of Patent: Jun. 13, 2023

(54) SEPARABLE PACKAGE

(71) Applicant: Church & Dwight Co., Inc., Princeton, NJ (US)

(72) Inventors: William D. Platt, Lumberton, NJ (US); Caryn Culleton Oryniak, Hillsborough, NJ (US); Richard James Elliott Gilbert, Belle Mead, NJ (US); Jonathan Andrew Wharton, Ewing, NJ (US); Gerhart P. Huy, Hamilton Square, NJ (US); Michael T. Pinchiaroli, Martinsville, NJ (US); Rajesh Ranjan, Irvine, CA (US); Velissa Van Scoyoc, Philadelphia, PA (US); David Schweitzer, Weston, CT (US); Jacob Daniel Taylor, Chicago, IL (US)

(73) Assignee: Church & Dwight Co., Inc., Princeton, NJ (US)

( * ) Notice: Subject to any disclaimer, the term of this patent is extended or adjusted under 35 U.S.C. 154(b) by 164 days.

(21) Appl. No.: 16/915,383

(22) Filed: Jun. 29, 2020

(65) Prior Publication Data
US 2021/0009334 A1    Jan. 14, 2021

Related U.S. Application Data

(60) Provisional application No. 62/873,424, filed on Jul. 12, 2019.

(51) Int. Cl.
*B65D 81/32* (2006.01)
*B65D 85/08* (2006.01)
(Continued)

(52) U.S. Cl.
CPC ...... *B65D 81/3205* (2013.01); *B65D 17/4011* (2018.01); *B65D 35/10* (2013.01);
(Continued)

(58) Field of Classification Search
CPC .... B65D 85/08; B65D 35/10; B65D 17/4011; B65D 81/3205; B65D 21/064;
(Continued)

(56) References Cited

U.S. PATENT DOCUMENTS

| 1,726,143 A | 8/1929 | Eisinger |
| 3,514,029 A | 5/1970 | Powell |

(Continued)

FOREIGN PATENT DOCUMENTS

| BE | 1015797 | 9/2005 | |
| DE | 102007039837 A1 * | 2/2009 | ............ A61F 6/005 |
| WO | WO-2013084007 A1 * | 6/2013 | ............ A61B 50/33 |

*Primary Examiner* — Rafael A Ortiz
(74) *Attorney, Agent, or Firm* — Church & Dwight Co., Inc.

(57) ABSTRACT

The present disclosure provides packages that are configured for containing a prophylactic device and a quantity of lubricant material. The package can include a first portion defining a first chamber containing a prophylactic device; and a second portion defining a second chamber containing a quantity of lubricant composition; wherein the first chamber of the first portion and the second chamber of the second portion are arranged to separably engage one another about external surfaces of the first portion and the second portion so as to form a unitary package. The present disclosure further provides methods for providing a lubricated prophylactic device.

17 Claims, 6 Drawing Sheets

(51) Int. Cl.
 *B65D 35/10* (2006.01)
 *B65D 17/28* (2006.01)
(52) U.S. Cl.
 CPC ...... *B65D 85/08* (2013.01); *B65D 2517/0013* (2013.01); *B65D 2517/0031* (2013.01)
(58) Field of Classification Search
 CPC ............ B65D 21/0219; B65D 21/0209; B65D 81/3216; A51F 6/005
 USPC .......................................... 206/69; 220/4.27
 See application file for complete search history.

(56) References Cited

U.S. PATENT DOCUMENTS

| | | | |
|---|---|---|---|
| D263,283 S | 3/1982 | Ronayne | |
| D274,792 S | 7/1984 | Price | |
| D370,846 S | 6/1996 | Hanna | |
| 5,685,420 A | 11/1997 | Martin et al. | |
| D445,673 S | 7/2001 | Richardson | |
| D472,803 S | 4/2003 | Saunders | |
| D520,185 S | 5/2006 | Zeng et al. | |
| 7,686,160 B2 | 3/2010 | Newman | |
| 7,938,256 B2 | 5/2011 | Nikitczuk et al. | |
| D642,463 S | 8/2011 | Schedl et al. | |
| 8,061,897 B2* | 11/2011 | Ichikawa | B65D 75/5855 383/35 |
| D651,096 S | 12/2011 | Nakagiri | |
| D655,201 S | 3/2012 | Schuch | |
| D662,584 S | 6/2012 | Browder | |
| D663,402 S | 7/2012 | Hewson-Hyde et al. | |
| D682,670 S | 5/2013 | Gottschalk | |
| D682,671 S | 5/2013 | Gottschalk | |
| D683,209 S | 5/2013 | Gottschalk | |
| D686,922 S | 7/2013 | Davis et al. | |
| D737,691 S | 9/2015 | Abbott et al. | |
| D753,480 S | 4/2016 | Paton et al. | |
| D764,270 S | 8/2016 | Paton et al. | |
| D787,368 S | 5/2017 | Meyers | |
| D814,117 S | 3/2018 | Groning | |
| D825,847 S | 8/2018 | Wissmann | |
| D826,038 S | 8/2018 | Blanc | |
| D828,749 S | 9/2018 | Swegle et al. | |
| 10,273,037 B2 | 4/2019 | Pan et al. | |
| D854,924 S | 7/2019 | Ashiwa | |
| D865,510 S | 11/2019 | Mathias et al. | |
| D867,133 S | 11/2019 | Johnson et al. | |
| D867,137 S | 11/2019 | Johnson et al. | |
| D880,291 S | 4/2020 | Meizlish et al. | |
| D890,434 S | 7/2020 | Brown et al. | |
| D896,946 S | 9/2020 | Gobber et al. | |
| D920,094 S | 5/2021 | Purkey et al. | |
| 2003/0226567 A1 | 12/2003 | McCleskey et al. | |
| 2004/0238380 A1 | 12/2004 | Newman | |
| 2005/0045497 A1 | 3/2005 | Sample | |
| 2008/0210579 A1* | 9/2008 | Mallory | A61F 6/005 206/69 |
| 2009/0241966 A1* | 10/2009 | Gray | A61F 6/005 206/69 |
| 2010/0078032 A1* | 4/2010 | Sarros | A61F 6/04 206/69 |
| 2010/0236948 A1 | 9/2010 | Madigan et al. | |
| 2013/0062226 A1* | 3/2013 | Lee | A61F 6/005 206/820 |
| 2013/0319425 A1* | 12/2013 | Osborne | A61F 6/005 221/133 |
| 2015/0001106 A1 | 1/2015 | Chopdat et al. | |
| 2015/0129437 A1 | 5/2015 | Clamp et al. | |
| 2015/0144141 A1* | 5/2015 | Mo | B65D 75/5838 206/69 |
| 2016/0374849 A1* | 12/2016 | Nguyen | B65B 25/146 128/844 |
| 2020/0093875 A1* | 3/2020 | McGowan | A61K 31/352 |

* cited by examiner

SEPARABLE PACKAGE

CROSS-REFERENCE TO RELATED APPLICATIONS

This application claims priority to U.S. Provisional Application No. 62/873,424, filed Jul. 12, 2019, and entitled, "A SEPARABLE PACKAGE," which application is incorporated by reference in its entirety herein.

FIELD OF THE DISCLOSURE

The present disclosure relates to packages for containing multiple materials. More particularly, the present disclosure relates to a separable package configured to contain a prophylactic device and a lubricating material.

BACKGROUND

Prophylactics, or condoms, may be provided in a variety of different styles. For example, condoms are sold in both lubricated and non-lubricated forms (i.e., with or without a lubricant composition combined therewith). Lubricated condoms typically are sold with a lubricant pre-applied to one or both of an exterior surface and in interior surface of the condom. The lubricant may be configured for providing extra comfort and/or enhanced stimulation to one or both partners during sexual intercourse. Often, lubricant in excess of the pre-applied amount may be desired by the partners for various purposes, such as foreplay, heightened sensation, massage, or to relieve general vaginal dryness. Commonly, extra lubricant can be purchased separately in multiple use bottles.

Relying upon the provision of added lubricant via a supplementary bottle or other container can be, at a minimum, inconvenient, and can cause embarrassment in the unintended disclosure that an individual is carrying a container of personal lubricant. Sexual activity is often spontaneous, and although it is socially acceptable to ask a sexual partner if they have a condom prior to engaging in sexual activity, it is not as readily acceptable to ask the partner if they have personal lubricant for use in the spontaneous activity. Furthermore, the need and/or desire for personal lubricant may not become evident until after initiation of sexual activity, and accessing a lubricant container or being required to search for a lubricant container during sexual activity can be mood-destroying at the time of need. Accordingly, there is a need in the field for means of providing a reservoir of personal lubricant in tandem with a prophylactic such that the personal lubricant is discreetly provided, readily available, and easily accessible at the time of need.

SUMMARY OF THE DISCLOSURE

The present disclosure provides a separable package configured to contain a prophylactic device and a lubricating material. The present disclosure includes, without limitation, the following example embodiments.

In one example embodiment, a package comprising: a first portion defining a first chamber containing a prophylactic device; and a second portion defining a second chamber containing a quantity of lubricant composition; wherein the first chamber of the first portion and the second chamber of the second portion are arranged to separably engage one another about external surfaces of the first portion and the second portion so as to form a unitary package, is provided.

In some example embodiments of the package of any preceding example embodiment, or any combination of any preceding example embodiments, each of the first portion and the second portion may comprise a backing layer defining the external surface thereof and a sealing layer engaging the backing layer so as to form the first chamber and the second chamber respectively.

In some example embodiments of the package of any preceding example embodiment, or any combination of any preceding example embodiments, the sealing layer may comprise a foil sealing layer or a plastic sealing layer.

In some example embodiments of the package of any preceding example embodiment, or any combination of any preceding example embodiments, the sealing layer may be a peel-off layer or a frangible layer.

In some example embodiments of the package of any preceding example embodiment, or any combination of any preceding example embodiments, the sealing layer may be removable and re-sealable to the backing layer of one or both of the first portion and the second portion.

In some example embodiments of the package of any preceding example embodiment, or any combination of any preceding example embodiments, the first portion containing the prophylactic device may include a first backing layer and a first sealing layer engaging the first backing layer so as to define the first chamber and contain the prophylactic device within, the prophylactic device being dispensable from the first chamber upon at least partial removal of the first sealing layer from the first backing layer, and wherein the second portion containing the quantity of lubricant composition may include a second backing layer and a second sealing layer engaging the second backing layer so as to define the second chamber and contain the quantity of lubricant composition within, at least a portion of the quantity of lubricant composition being dispensable from the second chamber upon compression of the second chamber about the external surface of the second portion such that the engagement of the second sealing layer with the second backing layer is at least partially broken.

In some example embodiments of the package of any preceding example embodiment, or any combination of any preceding example embodiments, the second chamber may include a dispensing zone in fluid communication with the second chamber and through which at least a portion of the quantity of lubricant composition is dispensable in response to compression of the second chamber about the external surface of the second portion such that the engagement of the second sealing layer with the second backing layer is at least partially broken about the dispensing zone.

In some example embodiments of the package of any preceding example embodiment, or any combination of any preceding example embodiments, the external surface of one of the first portion and the second portion may define a depression that separably engages a protrusion defined by the external surface of the other one of the first portion and the second portion so as to form the unitary package.

In some example embodiments of the package of any preceding example embodiment, or any combination of any preceding example embodiments, the external surface of the first portion may define the depression formed as an annular ring or congruent shape that separably engages the protrusion defined by the external surface of the second portion.

In some example embodiments of the package of any preceding example embodiment, or any combination of any preceding example embodiments, the external surface of the second portion may define the depression formed as an annular ring that separably engages the protrusion defined by the external surface of the first portion.

In some example embodiments of the package of any preceding example embodiment, or any combination of any preceding example embodiments, the prophylactic device may comprise a condom or a pre-lubricated condom.

In some example embodiments of the package of any preceding example embodiment, or any combination of any preceding example embodiments, the unitary package may be separable into the first portion and the second portion upon disengagement of the external surfaces of the first portion and the second portion.

In some example embodiments of the package of any preceding example embodiment, or any combination of any preceding example embodiments, the package may further comprise a third portion defining a third chamber comprising one of a second prophylactic device and a second quantity of lubricant composition, the third portion being separably coupled to the first portion; and a fourth portion defining a fourth chamber comprising the other one of the second prophylactic device and the second quantity of lubricant composition, the fourth portion being separably coupled to the second portion; wherein the coupled first and third portions and the coupled second and fourth portions may be arranged so that the first chamber of the first portion and the second chamber of the second portion separably engage one another about external surfaces of the first portion and the second portion, and such that the third chamber of the third portion and the fourth chamber of the fourth portion separably engage one another about external surfaces of the third portion and the fourth portion so as to form the unitary package.

In another example embodiment, a method of providing a lubricated prophylactic device comprising: containing a prophylactic device within a first chamber of a first portion; containing a quantity of lubricant composition within a second chamber of a second portion; and separably engaging the first chamber of the first portion and the second chamber of the second portion about external surfaces of the first portion and the second portion so as to form a unitary package, is provided.

In some example embodiments of the method of any preceding example embodiment, or any combination of any preceding example embodiments, one or both of containing the prophylactic device within the first chamber and containing the quantity of lubricant composition within the second chamber respectively may comprise engaging a first backing layer defining the external surface of the first portion with a first sealing layer so as to form the first chamber with the prophylactic device contained within, and engaging a second backing layer defining the external surface of the second portion with a second sealing layer so as to form the second chamber with the quantity of lubricant composition contained within.

In some example embodiments of the method of any preceding example embodiment, or any combination of any preceding example embodiments, one or both of engaging the first backing layer with the first sealing layer and engaging the second backing layer with the second sealing layer may comprise engaging a removable and re-sealable sealing layer with one or both of the first and second backing layers.

In some example embodiments of the method of any preceding example embodiment, or any combination of any preceding example embodiments, one or both of engaging the first backing layer with the first sealing layer and engaging the second backing layer with the second sealing layer may comprise engaging a foil sealing layer or a plastic sealing layer with one or both of the first and second backing layers.

In some example embodiments of the method of any preceding example embodiment, or any combination of any preceding example embodiments, one or both of engaging the first backing layer with the first sealing layer and engaging the second backing layer with the second sealing layer may comprise engaging a peel-off layer or a frangible layer with one or both of the first and second backing layers.

In some example embodiments of the method of any preceding example embodiment, or any combination of any preceding example embodiments, the method may further comprise one or both of: at least partially removing the first sealing layer from the first backing layer so as to dispense the elastomeric material from the first chamber; and compressing the second chamber about the external surface of the second portion such that the engagement of the second sealing layer with the second backing layer is at least partially broken about a dispensing zone in fluid communication with the second chamber and so as to dispense at least a portion of the quantity of lubricant composition from the dispensing zone.

In some example embodiments of the method of any preceding example embodiment, or any combination of any preceding example embodiments, separably engaging the first chamber of the first portion and the second chamber of the second portion may comprise separably engaging a depression defined by the external surface of the first portion and the second portion with a protrusion defined by the external surface of the other one of the first portion and the second portion so as to form the unitary package.

In some example embodiments of the method of any preceding example embodiment, or any combination of any preceding example embodiments, the method may further comprise disengaging the external surfaces of the first portion and the second portion of the unitary package to separate the unitary package into the first portion and the second portion.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure or recited in any one or more of the claims, regardless of whether such features or elements are expressly combined or otherwise recited in a specific embodiment description or claim herein. This disclosure is intended to be read holistically such that any separable features or elements of the disclosure, in any of its aspects and embodiments, should be viewed as intended to be combinable, unless the context of the disclosure clearly dictates otherwise.

DETAILED DESCRIPTION OF THE DISCLOSURE

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to packaging useful for the common provision of a prophylactic device, particularly a condom or a pre-lubricated condom, and a quantity of at least one personal lubricant composition. The quantity of the at least one personal lubricant composition in particular is commonly packaged but stored separately from the prophylactic device until the time of use. As such, the at least one personal lubricant composition specifically is not provided pre-applied to the prophylactic device; although, the prophylactic device may be pre-lubricated, such that the prophylactic device is lubricated with a lubricant composition (different than or similar to the lubricant composition of the package) prior to application of the lubricant composition of the package to the prophylactic device.

Packaging for condoms is typically configured to be minimal and discreet. Often, the condom is packaged between sheets of a heat sealable laminated film of aluminum foil, plastic, and/or paper. As such, the package is typically configured to be torn or cut open for removal of the condom, and the package itself provides little or no use other than storing the unused condom. The presently disclosed packages are adapted to or configured to not only provide protective storage of the condom but also provide conveniently accessible storage of a personal lubricant that can be dispensed onto the condom prior to or during use and/or for disposing of the condom after use. Moreover, the presently disclosed packages provide unitary storage of the condom as well as personal lubricant provided therewith, and the separate storage can be adapted to or configured to allow for easy dispensing of the lubricant onto the condom.

Figure 1:
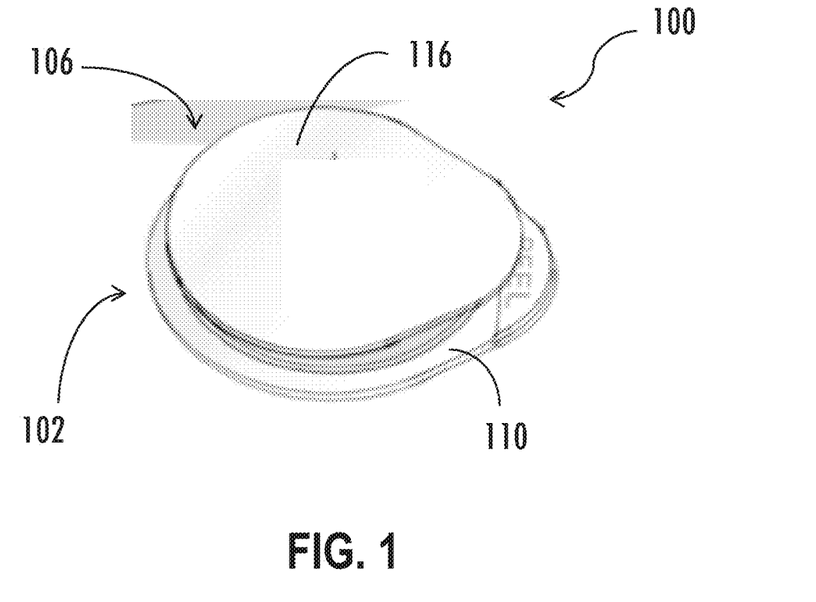
FIG. 1 illustrates a perspective view of a package including a first portion containing a prophylactic device and a second portion containing a quantity of lubricant composition, the first portion and the second portion being engaged one with the other according to an example embodiment of the present disclosure.
Figure 2:
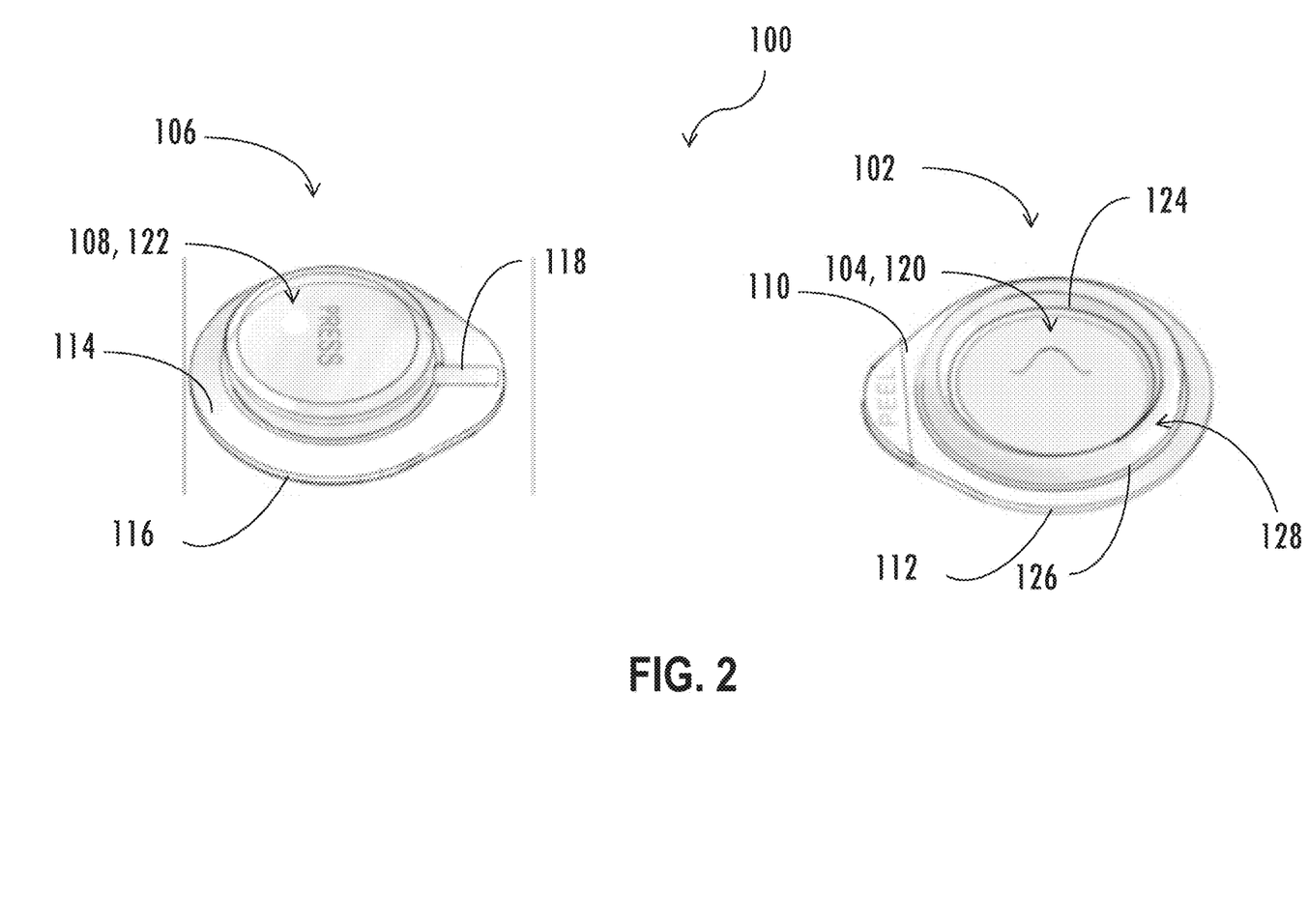
FIG. 2 illustrates a further view of the package of FIG. 1 where the first portion and the second portion are separated from one another.

Referring to FIG. 1, a package 100 according to embodiments of the present disclosure can comprise a first portion 102 defining a first chamber 104 (see FIG. 2). The first chamber 104 can be sized and shaped to contain therein or more prophylactic device, such as a condom. More particularly, the first chamber 104 can comprise one condom, two condoms, three condoms, etc., where the condoms can be the same size, shape, color, texture, etc., or may differ and can be nested within one another. The package 100 can also comprise a second portion 106 defining a second chamber 108 (see FIG. 2). The second chamber 108 can be sized and shaped to contain therein a quantity of lubricant composition. Additional chambers, such as a third chamber, a fourth chamber, a fifth chamber, a sixth chamber, etc., can also be included in the package 200 (see FIGS. 4A and 4B). Any of the additional chambers may be sized and shaped to include additional prophylactic devices or further quantities of lubricant composition, which may be the same as or different than the prophylactic device and quantity of lubricant composition contained in the first chamber 104 and/or the second chamber 108.

The quantity of lubricant composition provided in the second chamber 108 can be any type of personal lubricant composition. For example, U.S. Patent Publication No. 2018/0153800 to Church & Dwight Co. Inc., the disclosure of which is incorporated herein by reference, discloses lubricant compositions configured for providing sensations, such as warming, cooling, tingling, refreshing, and/or numbing, and any of such compositions can be suitable for use according to the present disclosure. As an example embodiment, the second chamber 108 may include a personal lubricant composition that is configured to provide a warming effect and/or a cooling effect. In further embodiments, the personal lubricant included in the package 100 may be configured to provide one or more flavors, sensations, and/or aromas. As such, the personal lubricant may be individually dispensed at the time of use of the condom contained in the first chamber 104. In some example embodiments, the first chamber 104 of the first portion 102 and the second chamber 108 of the second portion 106 are arranged to separably engage one another about external surfaces of the first portion 102 and the second portion 106 so as to form a unitary package. A "unitary package" as used herein, is defined as the first portion 102 and the second portion 106 forming a single or uniform entity, the entity being separable upon application of the required pressure necessary. For example the first portion 102 and the second portion 106 may engage one another to form the unitary package by press fit engagement. However, other types of engagement (e.g., magnetic engagement, adhesive engagement, or threaded engagement) of the first portion 102 and the second portion 106 are contemplated herein.

Each of (or one of) the first portion 102 and the second portion 106 may comprise a backing layer defining the external surface thereof and a sealing layer engaging the backing layer so as to form the first chamber 104 and the second chamber 108 respectively. The sealing layer and the backing layer of the first portion 102 and the second portion 106 may be the same materials or different materials. The backing layer may comprise, in some example embodiments, a polymeric material that may be shaped to receive either the prophylactic device or the quantity of lubricant composition. In certain example embodiments, the backing layer therefore may be formed from a polymeric material that may be extruded, thermoformed, or otherwise manufactured into a desired shape. The sealing layer may comprise a variety of different materials. In some example embodiments, the sealing layer may comprise a foil sealing layer, a foil-lined paper sealing layer, a polymeric (e.g., plastic) sealing layer, or any type of similar layer. It is desirable that that material of both the sealing layer and the backing layer provides a barrier against any ingress into or egress out of the first and second chambers 102, 106.

Further, it is beneficial for the backing layer be formed of a material that can be adapted to or configured to exhibit a strength and/or a compression resistance. For example, the backing layer may be adapted to or configured to provide a self-sustaining rigidity for structural integrity of the overall package 100, which is sufficient to withstand the rigor of being handled and carried in clothing pockets, purses, satchels, and/or wallets without being punctured, torn, leaking, or otherwise allowing for release of the liquid lubricant composition. "Rigidity" as used herein, is understood to indicate that once provided in a final shape, the material is sufficiently strength to maintain the final shape at least under an applied pressure equal to its own weight. Thus, when the backing layer is provided in a defined shape, the defined shape will not collapse under its own weight.

Conversely, for example, the backing layer may be adapted to or configured to be sufficiently compressible to allow a male or female adult user to easily compress (i.e., with the fingers of an adult user) under average adult user conditions. In this manner, sufficient compression of the backing layer may actuate dispensing of the liquid lubricant composition without the requirement of excessive force. In other words, the backing layer of the first and/or second chamber(s) 104, 108 may be sufficiently strong such that the first and/or second chamber(s) 104, 108 may substantially resist unintended compression, while being sufficiently flexible to submit to a level of compression that is capable of being produced with the fingers of an average adult user. As such, the backing layer can be defined as being both compressible and exhibiting a self-sustaining rigidity.

Accordingly, in one or more example embodiments, the backing layer may be adapted to or configured to be sufficiently compressible to provide for dispensing of at least 50% by weight, at least 75% by weight, at least 90% by weight, or at least 95% by weight of the lubricant composition stored in the second chamber 108 through application of compression in the range of about 5 to about 200 pounds of thumb force (i.e., force applied by a digit such as the thumb), about 10 to about 175 pounds of thumb force, or about 15 to about 150 pounds of thumb force.

The backing layer and the sealing layer may be engaged with one another by crimping, heat sealing, or any other type of adhesive, such as, an epoxy glue. The type of engagement between the backing and sealing layer may determine the manner in which the sealing layer is removed from the backing layer. In some example embodiments, the sealing layer is a peel-off layer, which may be separated from the backing layer by pulling apart the sealing layer in order to provide access to the chamber within. For example, the peel-off sealing layer can be adapted to or configured to be completely removable from the backing layer of one or both of the first portion 102 and the second portion 106 without the ability to reapply the sealing layer thereto. In some other example embodiments, the sealing layer is a frangible layer and may be punctured to create an opening into the respective chamber or compressed to break the seal between the sealing layer and the backing layer in order to provide access to the contents of the chamber defined therein. A frangible layer is a layer that may be punctured to create an opening through the layer or otherwise disengaged from the backing layer (e.g., through pressure applied to the backing layer) in order to provide an opening between the backing layer and sealing layer.

Alternatively, in other examples, the peel-off sealing layer can be adapted to or configured to be removable or frangible and re-sealable to the backing layer of one or both of the first portion 102 and the second portion 106 by re-crimping, magnetic attraction, reusable adhesive, or the like. As such, the sealing layer can be at least partially removed or disengaged from the backing layer and then re-sealed to the backing layer. The ability to re-seal the sealing layer of the second portion 106 can reduce the opportunity for any lubricant composition that may be present in the second chamber 108 to leak therefrom after dispensing of the lubricant composition and before disposal of the package 100. Further, in some example embodiments, the used prophylactic may be replaced into the first chamber 104, and the sealing layer may be re-sealed to the backing layer of the first portion 102 for a substantially mess-free disposal. Still further, the first portion 102 may be discarded, while the re-sealed second portion 106 may be ready for use during another sexual encounter. Other manners of engaging and removing the sealing layer from the backing layer are contemplated herein in this disclosure.

In some example embodiments, the sealing layer and/or the backing layer may be formed of a material particularly suited for receiving words, symbols, colors, or other printing that can impart a nature of the material(s) contained within the package 100. For example, suitable printing can be applied on the sealing layer to identify the type of personal lubricant stored in the second chamber 108. Likewise, branding, the type of lubricant contained within, instructions for use, or other printing may be provided on the sealing layer of the first chamber 102 and/or the second chamber 108. For example, instructions such as, "peel", "pull", "press", "open", "squeeze", etc., may be printed, embossed, stamped, or otherwise applied to the backing layer (see, e.g., FIG. 2). Further, in some example embodiments, the sealing layer and/or the backing layer may be substantially transparent or may be substantially translucent so as to allow the adult user to view the contents contained within the respective portion 102, 106. Alternatively, the sealing layer and/or the backing layer may be substantially opaque. In another example embodiment, the sealing and/or backing layer may be substantially transparent in one or more regions and may be substantially translucent or substantially opaque in one or more regions.

As illustrated in FIG. 2, for example, the first portion 102 containing the prophylactic device may include a first backing layer 110 and a first sealing layer 112 engaging the first backing layer 110 so as to define the first chamber 104 and contain the prophylactic device within. The prophylactic device may be dispensable from the first chamber 104 upon at least partial removal of the first sealing layer 112 from the first backing layer 110 by, for example, peeling off the first sealing layer 112 to at least partially reveal an interior of the first chamber 104. Additionally, the second portion 106 containing the quantity of lubricant composition may include a second backing layer 114 and a second sealing layer 116 engaging the second backing layer 114 so as to define the second chamber 108 and contain the quantity of lubricant composition within. At least a portion of the quantity of lubricant composition may be dispensable from the second chamber 108 upon compression of the second chamber 108 about the external surface of the second portion 106 such that the engagement of the second sealing layer 116 with the second backing layer 114 is at least partially or substantially completely broken or disengaged from the second sealing layer 116. Alternatively, the portion of the quantity of lubricant composition may be dispensable from the second chamber 108 upon at least partial removal of the second sealing layer 116 from the second backing layer 114 by, for example, peeling off the second sealing layer 116 to at least partially reveal an interior of the second chamber 108 and allow partial access to the lubricant composition therein. Compression may then be applied to the second chamber 108 so that the quantity of lubricant composition is directed through an opening formed by at least partially removing the second sealing layer 116 or an adult users finger, condom, or other material may be able to directly access the quantity of lubricant composition in the second chamber 108.

More particularly, the backing layers 110, 114 may form the external surface of the first portion 102 and the second portion 106, respectively, and in conjunction with the sealing layers 112, 116 may define an interior having an interior volume of the first chamber 104 in which a condom or other prophylactic device may be stored or contained and an interior volume of the second chamber 108 in which a quantity of lubricant material may be stored or contained. One or more of the first chamber 102 and the second chamber 108 can be sized and shaped to contain a desired prophylactic device (e.g., in the first chamber 104) and/or a desired content of lubricant composition (e.g., in the second chamber 108). For example, in typical embodiments, the second chamber 108 can be sized to contain about 2.5 grams of liquid lubricant composition; although in some other embodiments, the second chamber 108 can be sized to contain about 0.25 grams to about 5 grams, about 0.3 grams to about 4 grams, or about 0.5 grams to about 3 grams of liquid lubricant composition. In further example embodiments, the second chamber 108 can be adapted to or configured to contain a broader predefined ranged amount of liquid lubricant that is predefined based upon one or more of an average amount of lubricant commonly utilized in a single sexual encounter, lubricant density, lubricant texture, lubricant viscosity, and lubricant sensational property or properties. In one or more example embodiments, the first chamber 104 can be adapted to or configured to contain a condom having an industry standard sizing (e.g., thin, regular, large, or magnum). The first chamber 104 may be sized to contain the condom and include an excess storage volume to accommodate rolling variances (e.g., so that the condom does not get inadvertently pinched during package sealing). This first chamber 104 may also be sized to accommodate a pre-lubricated condom, allowing the additional lubricant contained in the second chamber 108 to supplement the amount of lubricant on the pre-lubricated condom or to be used for foreplay or massage.

Dispensing of the lubricant composition from the second chamber 108 can be via a variety of pathways. As further described below, the package 100 can be configured so that the lubricant composition is dispensable through limited means in order to reduce accidental spills of the lubricant and/or to allow for more precise application of the lubricant to the condom stored in the first chamber 104. In some example embodiments, and as illustrated in FIG. 2, the second chamber 108 may include a dispensing zone 118 in fluid communication (i.e., to directly or indirectly receive and/or transport the lubricant composition along a length thereof) with the second chamber 108 and through which at least a portion of the quantity of the lubricant composition is dispensable. The dispensing zone 118 may be formed from the second backing layer 114 or a separate second backing layer in conjunction with the second sealing layer 116 or a separate second sealing layer. The second sealing layer so formed can be removable or frangible and re-sealable separately from the second backing member so formed.

The dispensing zone 118 may be formed as a channeled seal that, in particular, can be useful to maintain a sealing arrangement until the time of desired dispensing of the lubricant composition. The channeled seal can be a sealing arrangement that, when intentionally compromised, will desirably channel the lubricant composition to a desired location. As discussed above, a channeled seal (or other sealing arrangement) can be utilized to channel the lubricant composition from the second chamber 108 toward an exterior of the second portion 106. In some embodiments, however, a channeled seal (or other sealing arrangement) can be utilized to channel the contained lubricant composition away from the second chamber 108 through a first end and to second, opposing end defining a dispensing outlet that will allow the lubricant to flow with controlled action to an exterior location (e.g., a finger, a condom, or a sexual organ) where the lubricant can be utilized, for example, to promote foreplay, to provide sexual sensations, for massage, or to provide other eroticism before, during, or after a sexual act.

As illustrated the dispensing zone 118 terminates substantially at a perimeter of the second chamber 108. It is understood, however, that the dispensing zone 118 may extend a distance into the second chamber 108. For example, the dispensing zone 118 may extend into the second chamber a distance that is about 5% to about 45%, about 10% to about 45%, or about 15% to about 45% of the total width of the second chamber 108. With such distance, the dispensing zone 118 can be adapted to or configured to directly receive (though it may be configured to also indirectly receive) the lubricant composition and direct the lubricant composition from the second chamber 108 externally therefrom.

For example, the lubricant composition may be dispensed from the second chamber 108 in response to at least partial removal of the second sealing layer 116 from the second backing layer 114 and/or compression of the second chamber 108 about the external surface of the second portion 106. The dispensing zone 118 may be formed as a sub-chamber in fluid communication with the second chamber 108, such that compression of the second chamber 108 results in directing at least a portion of the quantity of the lubricant composition into the dispensing zone 118. Alternatively, at least partial removal of the second sealing layer 116 from the second backing layer 114 or puncturing of the second sealing layer 116, results in access to the portion of the quantity of the lubricant composition in the dispensing zone 118 or from the second chamber 108. In this manner, the dispensing zone 118 can substantially preclude the quantity of lubricant composition contained in the second chamber 108 from exiting the package 100 as the lubricant composition can be precisely dispensed from the dispensing zone 118.

In some example embodiments, the exterior surface formed by the first backing layer 110 and the second backing layer 114 of the first portion 102 and the second portion 106, respectively, may define one or more perimeters. The perimeters may extend from the exterior surface of the first and second backing layers 110, 114. In this manner, the perimeters may define an outer boundary of the first chamber 104 and the second chamber 108, respectively. The outer boundary of the first chamber 104 and the outer boundary of the second chamber 108 may be formed so that when the first portion 102 and the second portion 106 are engaged with one another, the outer boundaries complimentarily engage one another.

For example, the external surface of one of the first portion 102 and the second portion 106 may define a perimeter forming an inner boundary so that a depression is defined, the depression separably engaging a protrusion being defined by a perimeter forming an outer boundary of the external surface of the other one of the first portion 102 and the second portion 106 so as to form the unitary package 100. In particular, the inner boundary of the depression substantially corresponds to the outer boundary of the protrusion so that the protrusion is complimentarily received within the depression. Actual inner boundary dimensions and cavity/chamber depth dimensions are variable based on the exact condom size, and lubricant dose, but can vary from about 26 millimeter (mm) to about 32 mm in diameter for the outer boundary, with less than about a 1 mm difference in diameter for the inner boundary diameter, and with a typical corresponding depth of about 4 mm to about 8 mm. In some example embodiments, a chamfered undercut or dimpled protrusions ranging from about 0.5 mm to about 2.0 mm may aid in engaging the first and second portions 102, 106. In some embodiments, the outer boundary defining the protrusion may be a single wall that forms substantially a convex chamber (e.g., a dome-shaped chamber) to form the protrusion, while the inner boundary defining the depression may be a single wall that forms a concave chamber to form the depression.

For example, and as illustrated in FIG. 2, the external surface of the first portion 102 defines a depression 120 formed as an annular ring or congruent shape (e.g., oblong circle, oval, etc.) that separably engages a protrusion 122 defined by the external surface of the second portion 106. In this example, an inner boundary 124 of the first portion 102 forms an inner ring of the annular ring, while an outer perimeter formed concentrically outside from the inner perimeter and extending from the exterior surface defines an outer boundary 126 forming an outer ring of the annular ring. In this manner, the inner ring and the outer ring cooperate to form a first sub-chamber 128 of the first portion 102. The inner boundary 124 and the outer boundary 126 defining the first sub-chamber 128 may be a single wall that forms both the first sub-chamber 128 and the first chamber 104; these chambers 104, 128 may also be formed from two separate walls. Regardless, the first sub-chamber 128 may contain a rim of the prophylactic device, while an elongated portion or a remainder of the prophylactic device is contained within the first chamber 104.

In another example, not shown, the external surface of the second portion 106 defines a depression formed as an annular ring that separably engages a protrusion defined by the external surface of the first portion 102. In this example, an inner boundary of the second portion 106 forms an inner ring of the annular ring, while an outer perimeter formed concentrically outside from the inner perimeter and extending from the exterior surface defines an outer boundary forming an outer ring of the annular ring. In this manner, the inner ring and the outer ring cooperate to form a second sub-chamber of the second portion 106. The inner boundary and the outer boundary defining the second sub-chamber may be a single wall that forms both the second sub-chamber and the second chamber 108; these chambers 108, 128 may also be formed from two separate walls. Regardless, the second sub-chamber may contain a rim of the prophylactic device, while an elongated portion or a remainder of the prophylactic device is contained within second chamber 108.

Figures 3A, 3B, 3C:
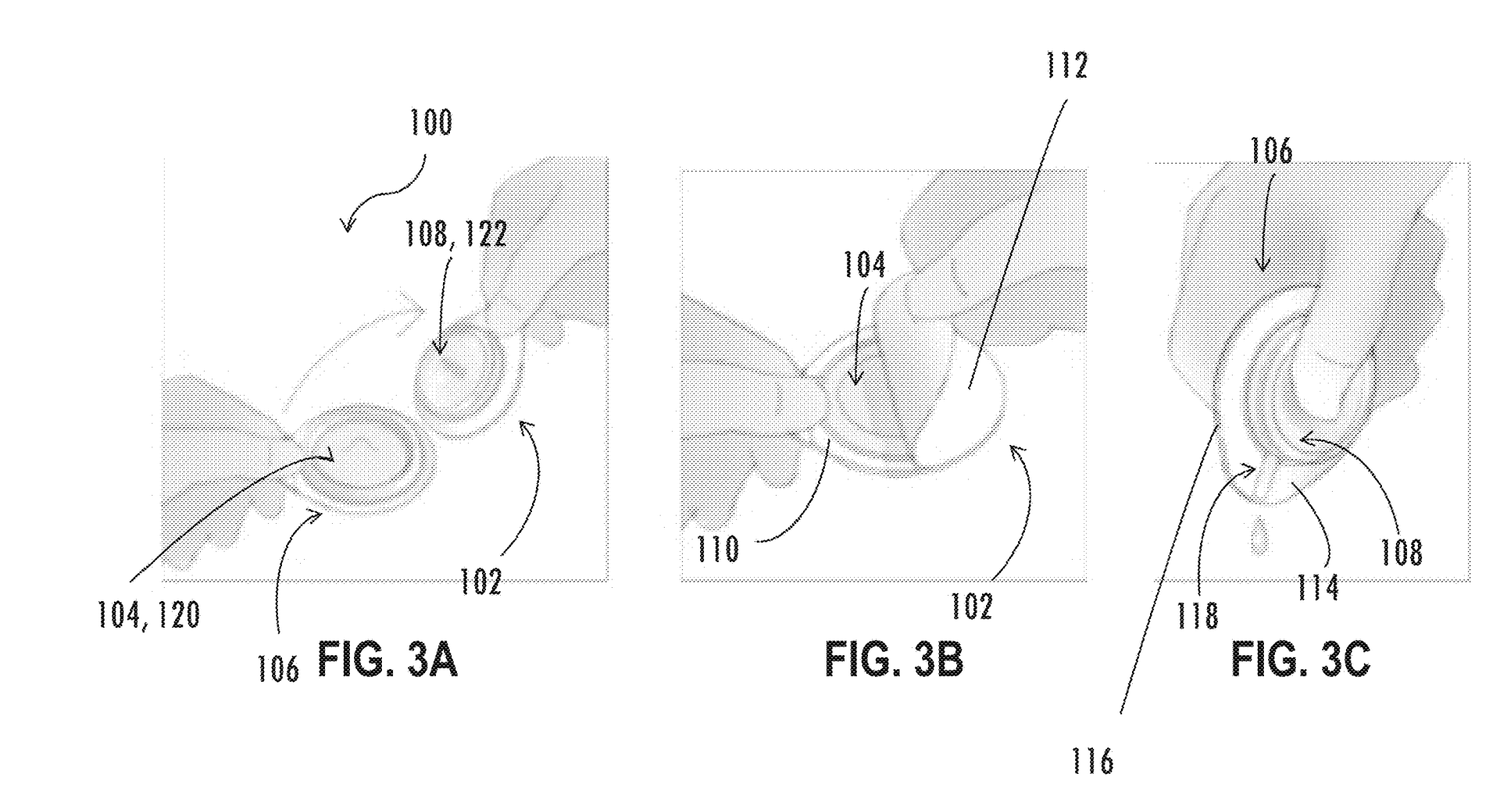
FIGS. 3A-3C illustrate a method of dispensing a prophylactic device and a lubricant composition according to an example embodiment of the present disclosure.

FIGS. 3A-3C illustrate an example method of dispensing a prophylactic device, such as a condom, and a lubricant composition. In particular, a package 100 as otherwise described herein can be provided with a condom contained in a first chamber 104 of a first portion 102 and a quantity of lubricant composition contained in a second chamber 108 of a second portion 106. In FIG. 3A, the unitary package 100 can be separated into the first portion 102 and the second portion 106 upon disengagement of the external surfaces of the first portion 102 and the second portion 106. More particularly, opposed force applied to each of the first portion 102 and the second portion 106 may overcome the engagement of the two portions, so that the unitary package 100 may be separated into the first and second portions 102, 106.

In FIG. 3B, the method can further include at least partially removing the first sealing layer 112 from the first backing layer 110 so as to dispense the prophylactic device from the first chamber 104. As illustrated in FIG. 3B, the first sealing layer 112 is a peel-off layer such that grasping the first sealing layer 112 and applying pressure in a direction away from the first backing layer 110 may result in separating the first sealing layer 112 from the first backing layer 110.

In FIG. 3C, the method can further include compressing the second chamber 108 with force sufficient to cause the quantity of lubricant composition contained therein to break the seal of the second sealing layer 116 or disengage from the second backing layer 114 so as to pass from the compressed second chamber 108 and into dispensing zone 118. As illustrated in FIG. 3C, the second sealing layer 116 is a frangible layer such that compressing the second sealing layer 116 about the external surface of the second portion 106 (i.e., in the region of the second chamber 108) results in at least partially breaking the frangible seal and enabling the quantity of lubricant to be dispensed to the dispensing zone. At such point, the quantity of lubricant composition may be dispensed from the dispensing zone 118 onto the prophylactic device, a finger, a hand, elsewhere, or a combination thereof. The second sealing layer 116 may also be a peel-off layer such that grasping the second sealing layer 116 and applying pressure in a direction away from the second backing layer 114 may result in separating the second sealing layer 116 from the second backing layer 114. In some example embodiments, the second sealing layer 116 may only be removed so as to expose the dispensing zone 118. As such, compression of the second chamber 108 may result in directing at least a portion of the quantity of the lubricant composition to the dispensing zone 118 for precise dispensing of that of portion of the lubricant material in the dispensing zone 118.

As previously noted, the first sealing layer 112 may be adapted to or configured to be re-sealable. As such, in some example embodiments, the method may comprise re-inserting the condom into the first chamber 104 and at least partially re-sealing the first sealing layer 112 over the opening of the first chamber 104 to the first backing layer 110. In addition, the method may comprise at least partially re-sealing the second sealing layer 116 over the opening of the second chamber 108 to the second backing layer 114. This can be beneficial to prevent leakage of unused personal lubricant from the second chamber 108 prior to discarding of the package 110.

Figure 4A:
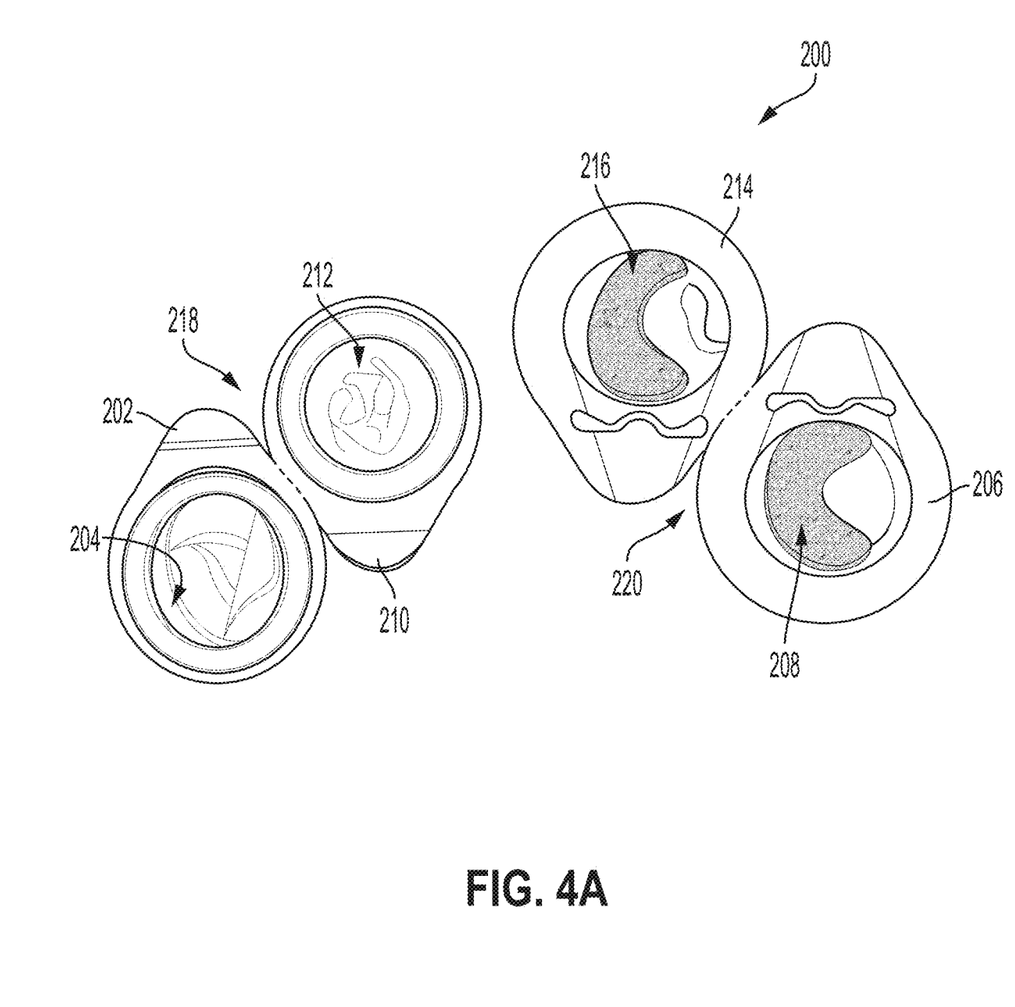
FIG. 4A illustrates a top planar view of a package including first and third portions separably coupled to one another and second and fourth portions separably coupled to one another according to another example embodiment of the present disclosure.
Figure 4B:
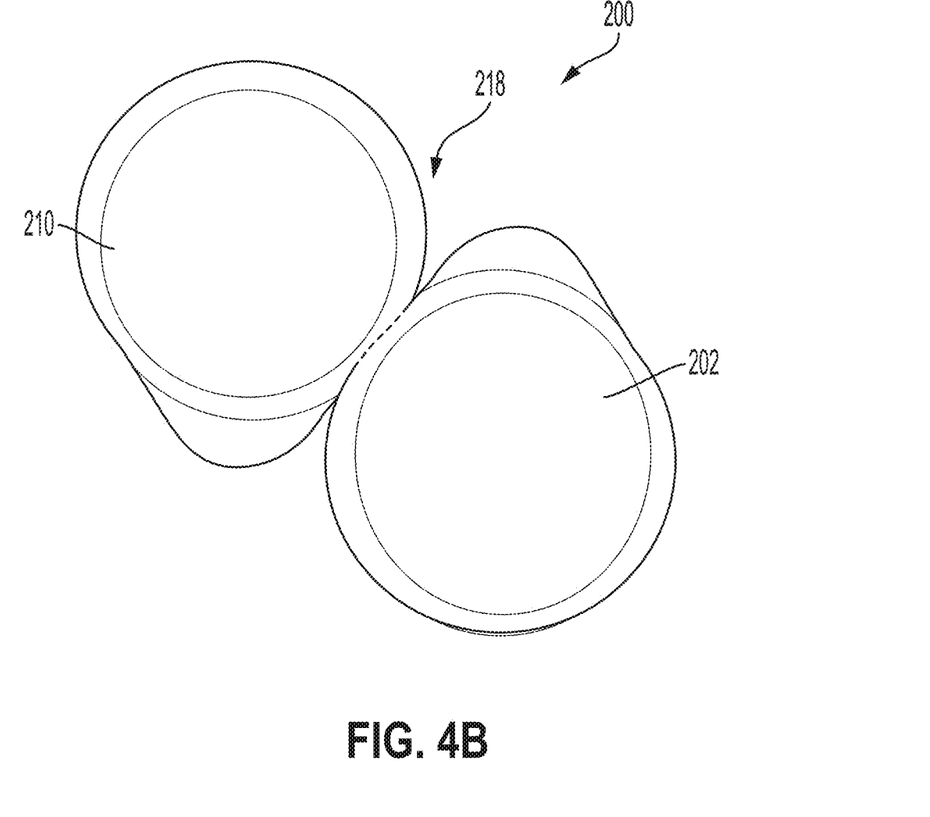
FIG. 4B illustrates a top planar view of the separably coupled first and third portions of the package of FIG. 4A, where the first portion and the second portion are separably engaged to one another and the third portion and the fourth portion are separably engaged to one another.

Referring now to FIGS. 4A and 4B, another example embodiment of a package 200 is illustrated. The package 200 can include the same or similar components as the package 100 illustrated in FIGS. 1-3C. For example, the package 200 can comprise a first portion 202 defining a first chamber 204. The package 200 can also comprise a second portion 206 defining a second chamber 208.

Further, the package 200 can comprise a third portion 210 defining a third chamber 212 comprising one of a second prophylactic device and a second quantity of lubricant composition. The third portion 210 can be separably coupled to the first portion 202. The package 200 can also comprise a fourth portion 214 defining a fourth chamber 216 comprising the other one of the second prophylactic device and the second quantity of lubricant composition. The fourth portion 214 can be separably coupled to the second portion 206. As illustrated in FIG. 4A, the first chamber 204 and the third chamber 212 can be sized and shaped to contain therein one or more prophylactic device, such as a condom. The second chamber 208 and the fourth chamber 216 can be sized and shaped to contain therein a quantity of lubricant composition.

In some embodiments, the separable coupling of each of the two portions may be accomplished by one of several different manners, such as, for example, a magnetic attraction, an adhesive, a perforation, crimping, and the like. As illustrated in FIG. 4A, for example, the first portion 202 and the third portion 210 may be coupled to one another by a perforation 218 about the edges of each of the first portion 202 and the third portion 210, while the second portion 206 and the fourth portion 214 may also be coupled to one another by a perforation 220 about the edges of each of the second portion 206 and the fourth portion 214.

The separably coupled portions 202, 210 and 206, 214 may be uncoupled from one another depending on the manner in which the portions are coupled. For example, where the coupling is by way of a perforation, tearing of the perforation may result in separating the two portions 202, 210 and 206, 214 without damaging the portions in any way.

In FIG. 4B, for example, the coupled first and third portions 202, 210 and the coupled second and fourth portions 206, 214 may be arranged so that the first chamber 204 of the first portion 202 and the second chamber 208 of the second portion 206 separably engage one another about external surfaces of the first portion 202 and the second portion 206, and such that the third chamber 212 of the third portion 210 and the fourth chamber 216 of the fourth portion 214 separably engage one another about external surfaces of the third portion 210 and the fourth portion 214 so as to form the unitary package 200. When the chambers are separably coupled and separably engaged with one another, a user may either simultaneously disengage the first chamber 204 and the second chamber 208, and the third chamber 212 and the fourth chamber 216 from one another so that the user is left with the coupled first and third portions 202, 210 and the coupled second and fourth portions 206, 214. Alternatively, the user may uncouple the first and third portions 202, 210 and the second and fourth portions 206, 214 from one another, so that the user is left with the engaged first and second chambers 204, 208 of the first and second portions 202, 206 and engaged third and fourth chambers 212, 216 of the third and fourth portions 210, 214.

Figure 5:
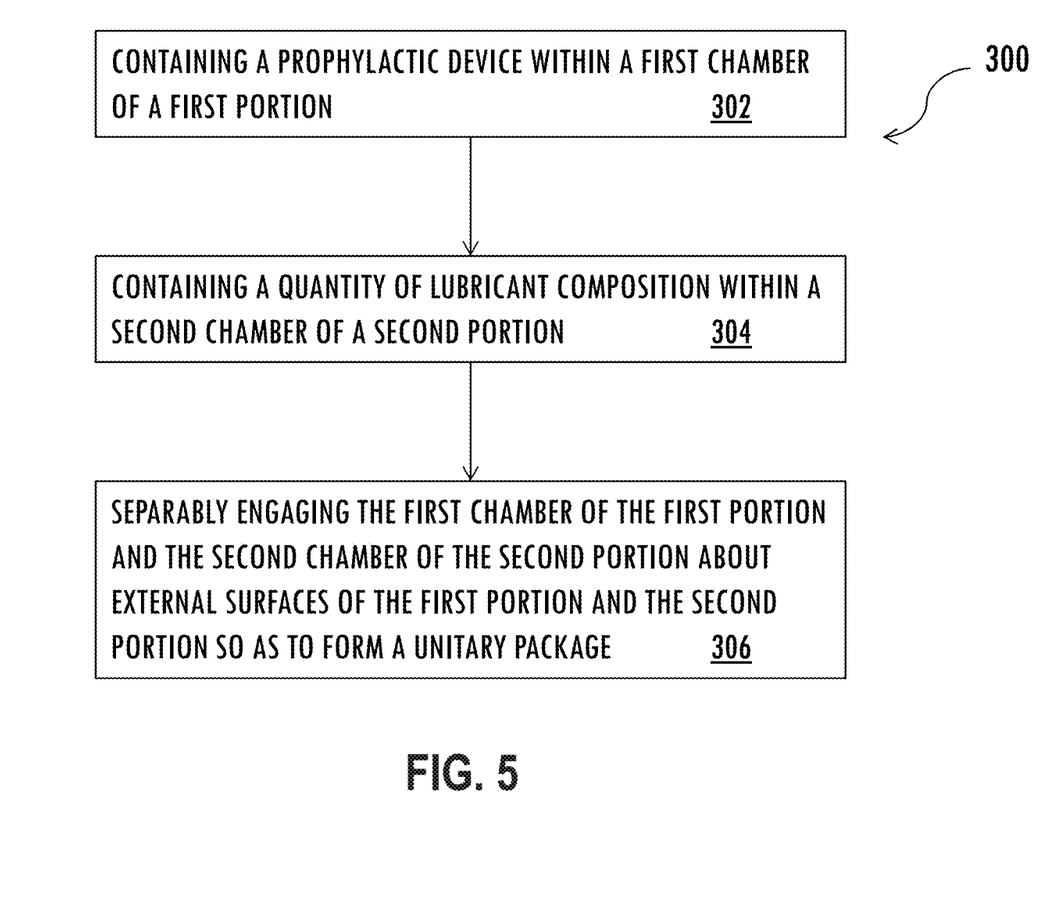
FIG. 5 is a flow chart illustrating a method of providing, in combination, a prophylactic device and a lubricant composition in separate packaging portions.

Alternatively, a sealing layer of the third portion 210 may be coupled to a sealing layer of the first portion 202 and a sealing layer the fourth portion 214 may be coupled to a sealing layer of the second portion 206. In this example embodiment, the coupled third portion 210 and first portion 202, and the coupled fourth portion 214 and second portion 206 may be respectively uncoupled from one another without impacting the respective sealing layers. For example, magnetic engagement may couple the respective sealing layers of the first and third portions 202, 210 and the second and fourth portions 206, 214 to one another. As a result, the coupled first and third portions 202, 210 and coupled second and fourth portions 206, 214 may then be removably engaged with one another, by either the first and second portions 202, 206 removably engaging one another about respective backing layers or the third and fourth portions 210, 214 removably engaging one another about respective backing layers. However, any other manner of coupling or engaging additional portions to the first and second portions 202, 206 is contemplated herein FIG. 5 provides a flow chart, generally designated 300, of chart illustrating a method of providing, in combination, a prophylactic device and a lubricant composition in separate packaging portions of a package. The package and/or packaging portions in the method 300 may be the package and/or packaging portions and the elements thereof described in reference to FIGS. 1-4B, although the package may be another type of package. A first step 302 of the method 300 may include containing a prophylactic device within a first chamber of a first portion. A second step 304 of the method 300 may comprise containing a quantity of lubricant composition within a second chamber of a second portion. A third step 306 of the method 300 may comprise separably engaging the first chamber of the first portion and the second chamber of the second portion about external surfaces of the first portion and the second portion so as to form a unitary package.

Where various numerical values are modified herein with use of the word "about" it is understood that the values can mean the exact value stated. The stated value as modified by the word "about", however, can vary by a relatively small amount, such as +/−5%, +/−4%, +/−3%, +/−2%, or +/−1% of the exact value.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A package comprising:
a first portion defining a first chamber containing a prophylactic device; and
a second portion defining a second chamber containing a quantity of lubricant composition;
wherein the first chamber of the first portion and the second chamber of the second portion are arranged to separably engage one another about external surfaces of the first portion and the second portion so as to form a unitary package; and
wherein the external surface of the first portion defines a depression formed by an annular ring that separably and directly engages a protrusion defined by the external surface of the second portion so as to form the unitary package, the external surface of the protrusion of the second portion being received by and directly contacting the external surface of the depression of the first portion.

2. The package of claim 1, wherein each of the first portion and the second portion comprises a backing layer defining the external surface thereof and a sealing layer engaging the backing layer so as to form the first chamber and the second chamber respectively.

3. The package of claim 2, wherein the sealing layer comprises a foil sealing layer or a plastic sealing layer.

4. The package of claim 2, wherein the sealing layer is a peel-off layer or a frangible layer.

5. The package of claim 2, wherein the sealing layer is removable and re-sealable to the backing layer of one or both of the first portion and the second portion.

6. The package of claim 2, wherein the first portion containing the prophylactic device includes a first backing layer and a first sealing layer engaging the first backing layer so as to define the first chamber and contain the prophylactic device within, the prophylactic device being dispensable from the first chamber upon at least partial removal of the first sealing layer from the first backing layer, and
wherein the second portion containing the quantity of lubricant composition includes a second backing layer and a second sealing layer engaging the second backing layer so as to define the second chamber and contain the quantity of lubricant composition within, at least a portion of the quantity of lubricant composition being dispensable from the second chamber upon compression of the second chamber about the external surface of the second portion such that the engagement of the second sealing layer with the second backing layer is at least partially broken.

7. The package of claim 6, wherein the second chamber includes a dispensing zone in fluid communication with the second chamber and through which at least a portion of the quantity of lubricant composition is dispensable in response to compression of the second chamber about the external surface of the second portion such that the engagement of the second sealing layer with the second backing layer is at least partially broken about the dispensing zone.

8. The package of claim 1, wherein the external surface of the first portion defines the depression formed as an annular ring or congruent shape that separably engages the protrusion defined by the external surface of the second portion.

9. The package of claim 1, wherein the prophylactic device comprises a condom or a pre-lubricated condom.

10. The package of claim 1, wherein the unitary package is separable into the first portion and the second portion upon disengagement of the external surfaces of the first portion and the second portion.

11. A method of providing a lubricated prophylactic device comprising:
containing a prophylactic device within a first chamber of a first portion;
containing a quantity of lubricant composition within a second chamber of a second portion; and
separably engaging the first chamber of the first portion and the second chamber of the second portion about external surfaces of the first portion and the second portion so as to form a unitary package;
wherein separably engaging the first chamber of the first portion and the second chamber of the second portion comprises separably and directly engaging a depression formed by an annular ring and defined by the external surface of the first portion with a protrusion defined by the external surface of the second portion so as to form the unitary package, the external surface of the protrusion of the second portion being received by and directly contacting the external surface of the depression of the first portion.

12. The method of claim 11, wherein containing the prophylactic device within the first chamber comprises engaging a first backing layer defining the external surface of the first portion with a first sealing layer so as to form the first chamber with the prophylactic device contained within, and/or
wherein containing the quantity of lubricant composition within the second chamber comprises engaging a second backing layer defining the external surface of the second portion with a second sealing layer so as to form the second chamber with the quantity of lubricant composition contained within.

13. The method of claim 12, wherein engaging the first backing layer with the first sealing layer comprises engaging a removable and re-sealable sealing layer with the first backing layer, and/or
engaging the second backing layer with the second sealing layer comprises engaging a removable and re-sealable sealing layer with the second backing layer.

14. The method of claim 12, wherein engaging the first backing layer with the first sealing layer comprises engaging a foil sealing layer or a plastic sealing layer with the first backing layer, and/or
engaging the second backing layer with the second sealing layer comprises engaging a foil sealing layer or a plastic sealing layer with the second backing layer.

15. The method of claim 12, wherein engaging the first backing layer with the first sealing layer comprises engaging a peel-off layer or a frangible layer with the first backing layer, and/or
engaging the second backing layer with the second sealing layer comprises engaging a peel-off layer or a frangible layer with the second backing layer.

16. The method of claim 12, further comprising:
at least partially removing the first sealing layer from the first backing layer so as to dispense the elastomeric material from the first chamber; and/or
compressing the second chamber about the external surface of the second portion such that the engagement of the second sealing layer with the second backing layer is at least partially broken about a dispensing zone in fluid communication with the second chamber and so as to dispense at least a portion of the quantity of lubricant composition from the dispensing zone.

17. The method of claim 11, further comprising disengaging the external surfaces of the first portion and the second portion of the unitary package to separate the unitary package into the first portion and the second portion.

* * * * *